US006365671B1

(12) United States Patent
Lin et al.

(10) Patent No.: US 6,365,671 B1
(45) Date of Patent: Apr. 2, 2002

(54) COMPOSITIONS CONTAINING CYANATE ESTER AND AROMATIC COMPOUNDS HAVING IMPROVED HEAT RELEASE PROPERTIES

(75) Inventors: Bor-Sheng Lin, Berkeley Heights, NJ (US); Michael James Amone, Carmel, NY (US)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/603,504

(22) Filed: Jun. 26, 2000

Related U.S. Application Data

(63) Continuation-in-part of application No. 09/267,585, filed on Mar. 12, 1999, now Pat. No. 6,242,638.

(51) Int. Cl.$^7$ ................................................ C08F 12/02
(52) U.S. Cl. ..................... 525/55; 560/301; 560/130; 560/138; 560/140; 528/422; 525/437; 525/523; 525/419; 525/903
(58) Field of Search ................. 560/310, 130, 560/138, 140; 528/422; 525/437, 523, 419, 55, 903

(56) References Cited

U.S. PATENT DOCUMENTS

| | | | |
|---|---|---|---|
| 3,856,566 A | 12/1974 | Saunders .................... | 117/218 |
| 3,994,949 A | 11/1976 | Meyer et al. | |
| 4,107,442 A | 8/1978 | Quinn ......................... | 568/726 |
| 4,110,541 A | 8/1978 | Kinson ....................... | 568/725 |
| 4,117,018 A | 9/1978 | Cleveland et al. .......... | 568/726 |
| 4,223,171 A | 9/1980 | Mark et al. .................. | 568/726 |
| 4,988,780 A | 1/1991 | Das et al. .................... | 525/504 |
| 5,109,078 A | 4/1992 | Das et al. .................... | 525/504 |
| 5,149,863 A | 9/1992 | Shimp et al. ................ | 560/301 |
| 5,360,887 A | 11/1994 | Tsunemi et al. ............. | 528/97 |
| 5,420,342 A * | 5/1995 | Craig, Jr. et al. | |
| 5,714,419 A | 2/1998 | Choate ........................ | 442/136 |

FOREIGN PATENT DOCUMENTS

WO          97/30105          8/1997

OTHER PUBLICATIONS

Chem. Abstract 112:218046 for S. Ising et al., "Flammability resistance of non–brominated cyanate ester resins", Int. Sampe Symp. Exhib. (1989), 34(Tomorrow's Mater.: Today, Book 2), pp. 1326–1335.

Chem. Abstr. 123:58610 for L. Hamilton et al., "Photodegradation of high performance fibers", Text. Chem. Color. (1994), 26(12), pp. 39–45.

Patent Abstracts of Japan, vol. 018, No. 182, (3/94), for JP 05339342.

Patent Abstracts of Japan, vol. 1999, No. 04, (4/99) for JP 11012464.

* cited by examiner

*Primary Examiner*—Robert Dawson
*Assistant Examiner*—Kuo-Liang Peng
(74) *Attorney, Agent, or Firm*—Lyon & Lyon LLP; Kristen H. Neuman; James H. Shalek

(57) ABSTRACT

The present invention relates to compositions of matter containing aromatic cyanate ester containing at least two rings linked by a group containing an unsaturated group and selected aromatic hydroxyl compounds that exhibited improved heat release and curing properties. The present invention further relates to a process for preparing said compounds and cured articles resulting from curable mixtures thereof.

10 Claims, No Drawings

COMPOSITIONS CONTAINING CYANATE ESTER AND AROMATIC COMPOUNDS HAVING IMPROVED HEAT RELEASE PROPERTIES

This is a continuation-in-part of application Ser. No. 09/267,585 Mar. 12, 1999 now U.S. Pat. No. 6, 242,638.

This invention relates to novel compositions of matter containing aromatic cyanate ester compounds having at least two rings linked by an unsaturated group containing member and selected phenolic compounds, prepolymers and compositions thereof, and processes for making the same. The compositions can be employed in adhesives, composites, laminates and molding compositions. The compositions have particular utility for use in molded articles requiring flame-resistance, low peak heat release rates, such as interiors for aircraft and other transportation vehicles, and low total heat release rates without generating significant amounts of smoke.

BACKGROUND OF THE INVENTION

Phenolic cyanate esters have been described extensively in the art. U.S. Pat. No. 5,360,887, for example, describes a flame resistant thermosetting composition containing a monocyanate ester and a dicyanate ester of the formula

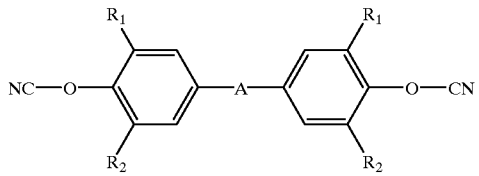

wherein the bridging member A can be a direct bond, methylene or mono- or disubstituted methylene with alkyl and/or an aryl group, or a five or six membered cycolalkylene, sulfonyl, thio, oxyl, carbonyl or xylylene. The teachings in U.S. Pat. No. 5,109,078 represent one of many teachings of cyanato-group containing phenolic resins of the formula:

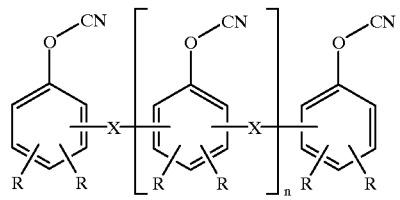

wherein X is a divalent organic radical, preferably a radical selected from the group consisting of: —CH2—, —CO—, —SO2—, (S)y,

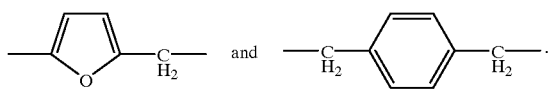

There is a need in the transportation industry, particularly for aircraft interiors, for molded polymeric components that exhibit very low peak heat release rates. Many cyanate esters exhibit good dielectric properties, water absorption and flame retardancy. However, all of the currently known cyanate esters fail to have heat release rates below 35 Joule/g-°K, more preferably below 10 Joule/g-°K. Low peak heat release rates can be attained using other high performance polymers such as polyphenylsulfone, polyamineimides, polybenzoimadazoles and polybenzoxazoles.

All of the currently available polymers having relatively low peak heat release rates suffer from one or more disadvantages such as high cost of manufacture or challenging processing requirements. The present invention produces molded articles having the desired low peak heat release rate using cyanate ester compounds and compositions thereof.

SUMMARY OF THE INVENTION

The present invention relates, in a first aspect, to a composition of matter containing
1) a selected cyanate ester compound represented by formula (I):

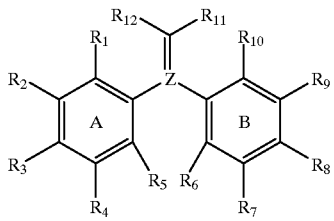

wherein
Z is $C_1$–$C_4$ alkylene group or a five or six membered cycolalkylene;
$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —NO$_2$, —NR'R", wherein R, R' and R" are H or $C_1$–$C_3$alkyl;
$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl;
$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —NO$_2$, —NR'R", wherein R, R' and R" are H or $C_1$–$C_3$alkyl; or
$R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
$R_{11}$ and $R_{12}$, independently of one another are H, phenyl, $C_1$–$C_4$alkyl or halogen; wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group;
2) up to about 15% by weight of selected aromatic hydroxy compounds having at least two rings having at least 6 carbon atoms per ring;
3) up to about 15% by weight of a halogenated compound according to formula II

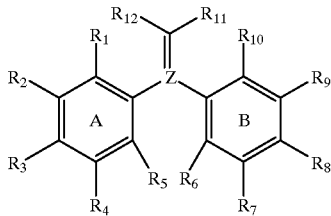

(II)

wherein

Z is $C_1$–$C_4$ alkylene group;

$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$, and $R_{12}$, independently of one another are H, phenyl, $C_1$–$C_4$alkyl or halogen; wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one hydroxyl group and at least one of $R_{11}$ and $R_{12}$ are a halogen group.

A preferred compound according to formula (I) is represented said formula where Z is $C_1$–$C_2$alkylene; $R_1$ and $R_{10}$ are H; $R_2$, $R_4$, $R_7$ and $R_9$, independently of one another, are halogen, H, OCN, or OH; $R_3$, $R_5$, $R_6$ and $R_8$, independently of one another, are H, OCN or OH; $R_{11}$ and $R_{12}$ are halogen; and at least one of aromatic rings A and B is substituted by at least one cyanato group.

A particularly preferred compound according to formula (I) is represented by said formula where Z is $C_1$–$C_2$alkylene; $R_1$, $R_5$, $R_6$ and $R_{10}$ are H; $R_2$, $R_4$, $R_7$ and $R_9$, independently of are halogen or H; $R_{11}$ and $R_{12}$ are halogen; and $R_3$ and $R_8$ are OCN. More preferably, $R_{11}$, and $R_{12}$ are chlorine or bromine. Most preferably, $R_{11}$, and $R_{12}$ are chlorine.

A further preferred compound is characterized according to formula (1) above wherein Z is methylene; $R_1$, $R_2$, $R_4$, $R_5$, $R_6$, $R_7$, $R_9$ and $R_{10}$ are H; $R_3$ and $R_8$ are OCN; and $R_{11}$ and $R_{12}$ are chlorine.

A preferred compound is characterized according to formula (11) above wherein Z is $C_1$–$C_2$alkylene; $R_1$ and $R_{10}$ are H; $R_2$, $R_4$, $R_7$ and $R_9$, independently of one another, are halogen, H, OCN, or OH; $R_3$, $R_5$, $R_6$ and $R_8$, independently of one another, are H, OCN or OH; $R_{11}$ and $R_{12}$ are halogen; and at least one of aromatic rings A and B is substituted by at least one hydroxyl group.

A particularly preferred compound is characterized according to formula (II) above wherein Z is $C_1$–$C_2$alkylene; $R_1$, $R_5$, $R_6$ and $R_{10}$ are H; $R_2$, $R_4$, $R_7$ and $R_9$, independently of one another, are halogen or H; $R_{11}$, and $R_{12}$ are halogen; and $R_3$ and $R_8$ are OH. More preferably, $R_{11}$, and $R_{12}$ are chlorine or bromine. Most preferably, $R_{11}$, and $R_{12}$ are chlorine.

A further preferred compound is characterized according to formula (II) above wherein Z is methylene; $R_1$, $R_2$, $R_4$, $R_5$, $R_6$, $R_7$, $R_9$ and $R_{10}$ are H; $R_3$ and $R_8$ are OH; and $R_{11}$ and $R_{12}$ are chlorine.

The present invention relates, in a second aspect, to a prepolymer mixture containing a cyclotrimerized reaction product of either the selected aromatic hydroxyl compound or compound according to formula 11 and at least one of compound according to formula (I) above. Preferably, up to about 60% of the cyanato groups in the overall mixture are trimerized as a part of the cyclotrimerized reaction product. More particularly, about 10 to 40%, preferably, about 20 to 30% of the cyanato groups in the overall composition are trimerized as a part of the cyclotrimerized reaction product.

The present invention, in a further aspect, relates to a composition containing a) a compound according to formula (I) above and b) a co-curing component selected from b1) a selected aromatic hydroxyl compound or b2) a compound according to formula (II) above or b3) mixtures thereof and c) a thermally curable monomer or oligomer other than a cyanate ester. Preferably, the thermally curable or reactive monomer or oligomer is selected from an epoxy, bismaleimide, polyimide, polyester, epoxy-acrylate, urethane-acrylate, diallyl phthalate, spiropyrane, phenolic resin and mixtures thereof.

The present invention, in a still further aspect, relates to a cured article resulting from a curable mixture comprising a compound according to formula (I) above or cyclotrimerized reaction product thereof and a co-curing component selected from a selected aromatic hydroxyl compounds or a compound according to formula II or mixtures thereof, wherein the cured article has a peak heat release rate of less than about 20 Joule/g-°K as measured using a pyrolysis-combustion flow calorimeter developed by the Federal Aviation Administration or a peak heat release rate of less than 30, preferably 25 as measured according to the Ohio State University heat release test. The present further relates to such cured article resulting having a total heat release of less than about 3 KJoule/g. The cured articles do not generate significant amounts of smoke during combustion.

DETAILED DESCRIPTION OF THE INVENTION

The present invention is a composition of matter containing a flame resistant aromatic cyanate ester compound, prepolymers thereof, and compositions containing the same, articles of manufacture, and methods of making and using the same. The compositions contain a compound having a linking group that contains an unsaturated group bridging at least two aromatic groups. More particularly, the compound can be represented by formula (I):

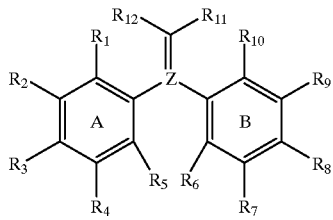

(I)

wherein

Z is $C_1$–$C_4$ alkylene group or a five or six membered cycolalkylene; $R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR ($C_1$–$C_3$alkyl), —NCOR($C_1$–$C_3$alkyl), —COR, —$NO_2$, —NR'R", wherein R, R' and R" are H or $C_1$–$C_3$alkyl;

$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;

$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;

$R_{11}$, and $R_{12}$, independently of one another are H, phenyl, $C_1$–$C_4$alkyl or halogen;

wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group.

In a more preferred compound, Z is $C_1$–$C_2$alkylene, $R_1$ and Rio are H; $R_2$, $R_4$, $R_7$ and $R_9$, independently of one another, are halogen, H, OCN, or OH; $R_3$ and $R_8$, independently, of one another, are H, OCN or OH; $R_5$ and $R_6$, independently of one anther, are H, OCN or OH; and $R_{11}$ and $R_{12}$ are halogen, wherein at least one of aromatic rings A and B is substituted by at least one cyanato group. In a particularly preferred compound, Z is $C_1$–$C_2$alkylene, $R_1$, $R_5$, $R_6$ and $R_{10}$ are H; $R_2$, $R_4$, $R_7$ and $R_9$, independently of one another, are halogen or H; $R_3$ and $R_8$ are OCN; and $R_{11}$ and $R_{12}$ are halogen. A most preferred compound is characterized by Z being methylene, $R_1$, $R_2$, $R_4$, $R_5$, $R_6$, $R_7$, $R_9$ and $R_{10}$ being H; $R_3$ and $R_8$ being a cyanato group and $R_{11}$ and $R_{12}$ being chlorine.

The compound according to formula I is prepared by reacting, in a first reaction, an aromatic compound substituted with a mono-, di- or tri-halogen containing aldehyde, acetal or hemiacetal or corresponding alcohol, in the presence of an acid, preferably a highly acidic environment having a pH of less than about 3, to produce an aromatic compound containing at least two rings linked by the halogen-substituted residue of the aldehyde, acetal or hemiacetal. In a second reaction, the resulting aromatic compound is contacted by a basic compound, such as potassium hydroxide, and an organic non-polar solvent, such as methanol, to remove at least one halogen group to produce an aromatic compound wherein the at least two rings are linked by a group containing an unsaturated group. The aforementioned reactions are described in greater detail in U.S. Pat. Nos. 3,856,566, 4,110,541, and 4,117,018, which are each incorporated herein by reference. In a third reaction, at least some of the hydroxyl groups of the aromatic compound resulting from the second reaction are converted into cyanato-groups via reaction with a cyanogenhalide, such as cyanogen chloride or cyanogen bromide, via a known reaction as described in U.S. Pat. No. 5,149,863 (which is incorporated herein by reference) to produce the desired final product. The resulting product can be used as is or recrystallized in purer form. The amount of cyanogenhalide should be sufficient to react with all of the hydroxyl groups of the aromatic compound resulting from the second reaction though greater or lesser than stoichiometric amounts can be employed.

Suitable aromatic compounds for this invention contain one or more aromatic rings having at least one hydroxyl group. The aromatic rings can be further substituted with alkyl and/or halogen groups. Examples of suitable aromatic compounds are phenol, phenyl phenol, cresol, xylenil, carvacol, thymol, naphthol, disubstituted naphthol, anthrol, phenanthrol, pyrocatechol, resorcinol, hydroquinone, and bicyclic hydroxyl-containing compounds linked by alkylene, carbonyl, oxyl, and/or sulfonyl groups and halogenated, such as bromine, fluorine and chlorine, corresponding compounds. It is anticipated that halogen substitution would improve the flame retardancy of molded articles resulting from such halogenated compounds and compositions thereof. Mixtures of said aromatic compounds can be used as well as mixtures with minor amounts of non-aromatic alcohols. Phenol is a particularly preferred aromatic compound for use herein.

Suitable halogen-containing aldehydes, acetals and hemiacetals include mono- and polyhalogenated compounds, such as fluoropropanal or fluoroacetaldehyde, bromopropanal or bromoacetaldehyde, chloroethanal, chloropropanal or chloroacetaldehyde, 2-chloro-1-ethoxy ethanol, 2-fluoro-1-ethoxy ethanol, 2-bromo-1-ethoxy ethanol, difluoropropanal or difluroacetaldehyde, dibromopropanal or dibromoacetaldehyde, dichloroethanal, dichloropropanal or dichloroacetaldehyde, 2,2-dichloro-1-ethoxy ethanol, 2,2-difluoro-1-ethoxy ethanol, 2,2-dibromo-1-ethoxy ethanol, trifluoropropanal or trifluoroacetaldehyde, tribromopropanal or tribromoacetaldehyde (bromal), trichloroethanal, trichloropropanal or trichloroacetaldehyde (chloral), 2,2,2-trichloro-1-ethoxy ethanol, 2,2,2-trifluoro-1-ethoxy ethanol, 2,2,2-tribromo-1-ethoxy ethanol. Trichloroethanal and 2,2,2-trichloro-1-ethoxy ethanol are particularly preferred.

A particularly preferred reaction sequence is exemplified below:

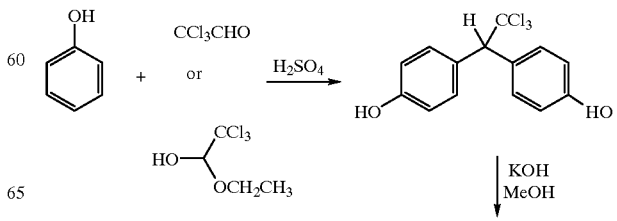

-continued

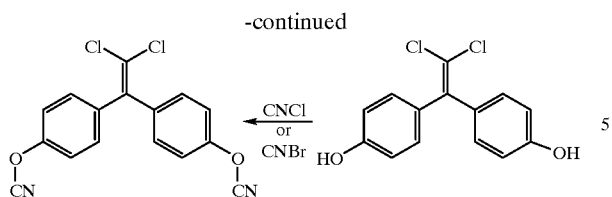

The novel compound described above forms, in conventional manner, an aromatic triazine network upon heating and/or in the presence of a curing agent. Typical curing conditions are from 120° C. to 250° C. at atmospheric to 500 psi pressure for 0.1 to 24 hours depending upon the sample size, temperatures, and pressures. The curing reaction is known as cyclotrimerization. At least three moles of cyanate ester monomer described above are required to produce one mole of cyclotrimerized prepolymer product. A composition containing the novel compound described above can be cyclotrimerized in conventional fashion to produce a prepolymer wherein up to about 60% of the cyanato groups in the overall composition have been trimerized. More preferably, the prepolymer is characterized by having about 10 to 40%, more preferably about 20 to 30% of the cyanato groups trimerized.

The compound described above forms a solid resin having a softening point in the range of 70 to 80° C.

The inventive composition further includes a co-curing component that is capable of lowering the curing temperature of the overall composition to less than 160° C. without significantly increasing the heat release rate. Particularly preferred co-curing components are selected from b1) aromatic hydroxy-containing compounds have at least two rings that are either fused or bonded via an organic or hetero linking group;

or b2) a compound according to formula (II)

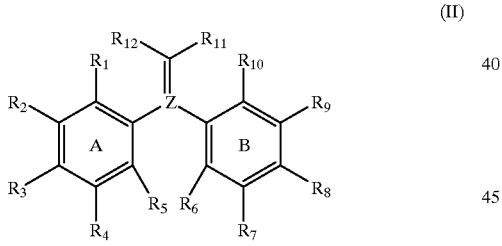

(II)

wherein
Z is $C_1$–$C_4$ alkylene group;
$R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR ($C_1$–$C_3$alkyl), —NCOR ($C_1$–$C_3$alkyl), —COR, —$NO_2$, —NR'R", wherein R, R' and R" are H or $C_1$–$C_3$alkyl;
$R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
$R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen; $R_{11}$, and $R_{12}$, independently of one another are H, phenyl, $C_1$–$C_4$alkyl or halogen; wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one hydroxyl group and at least one of $R_{11}$ and $R_{12}$ is a halogen group;

or mixtures thereof.

A preferred compound is characterized according to formula (11) above wherein Z is $C_1$–$C_2$alkylene; $R_1$ and $R_{10}$ are H; $R_2$, $R_4$, $R_7$ and $R_9$, independently of one another, are halogen, H, OCN, or OH; $R_3$, $R_5$, $R_6$ and $R_8$, independently of one another, are H, OCN or OH; $R_{11}$, and $R_{12}$ are halogen; and at least one of aromatic rings A and B is substituted by at least one hydroxyl group.

A particularly preferred compound is characterized according to formula (II) above wherein Z is $C_1$–$C_2$alkylene; $R_1$, $R_5$, $R_6$ and $R_{10}$ are H; $R_2$, $R_4$, $R_7$ and $R_9$, independently of one another are halogen or H; $R_{11}$, and $R_{12}$ are halogen; and $R_3$ and $R_8$ are OH. More preferably, $R_{11}$ and $R_{12}$ are chlorine or bromine. Most preferably, $R_{11}$, and $R_{12}$ are chlorine.

A further preferred compound is characterized according to formula (II) above wherein Z is methylene; $R_1$, $R_2$, $R_4$, $R_5$, $R_6$, $R_7$, $R_9$ and $R_{10}$ are H; $R_3$ and $R_8$ are OH; and $R_{11}$ and $R_{12}$ are chlorine.

Preferred aromatic hydroxyl-containing compounds are aromatic compounds having 2 or 3 rings having at least one hydroxyl group per molecule. Such preferred compounds are represented by the formulae

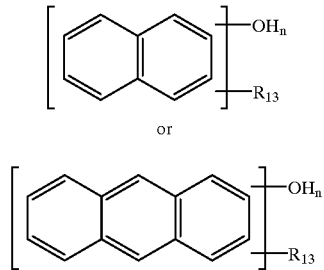

or

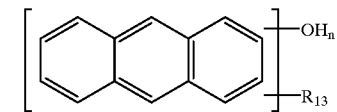

wherein n is a number from 1 to 4, more preferably 1 to 2, and $R_{13}$ is a halogen, preferably bromine or chlorine, methyl, ethyl, methoxy or ethoxy. Examples of such compounds include naphthol, methyl naphthol, (di)chloro naphthol, methoxy naphthol, (di)bromo naphthol, dihydroxy naphthalene, anthrarobin, phenanthrol. Naphthol is particularly preferred.

Further preferred aromatic hydroxyl-containing compounds are have two or three aromatic rings that are bonded via a linking group. Preferred linking groups are a direct bond, methylene or mono- or disubstituted methylene with alkyl and/or an aryl group, or a five or six membered cycolalkylene, sulfonyl, thio, oxyl, carbonyl or xylylene. One or more of the aromatic rings can be substituted with a halogen, methyl, ethyl, methoxy or ethoxy group. Examples of such compounds are dihydroxy methane, phenoxyphenol, (bromo)phenylphenol, (chloro)phenylphenol, biphenol, diphenylphenol, phenylhydroquinone, hydroxydiphenylmethane, cumylphenol, bis (hydroxyphenyl)methane, isopropylidenephenol, isopropylidene bis-dibromophenol, and tris-hydroxyphenolethane.

The compositions described above can contain other mono- and polycyanato-group containing compounds to form thermosetting resin compositions. The additional cyanato-group containing compounds can be halogenated in order to improve flame retardancy.

The compositions described above can also be combined with other thermal curable monomers and reactants, such as epoxies, bismaleimides, polyimides, polyesters, epoxyacrylates, urethane-acrylates, diallyl phthalates, spiropyrane, and phenol provided the molded article retains the desired low heat release characteristics. The composition can also contain a curing catalyst, such as imidazole compounds, tertiary amines or organometallic compounds. Organometallic compounds such as cobalt octanate, zinc octanate, cobalt naphthalenate, or zinc naphthenate are preferred. The composition can also further contain a filler such as alumina, aluminum hydroxide, antimony tri- or pentaoxide, zinc oxide, titanium dioxide, silica powder, quartz powder, glass powder, ceramic microballons or mixtures thereof.

A preferred thermosetting composition or resin varnish contains at least 30%, more preferably 50 to 100%, most preferably 60 to 99% by weight of the composition described above and/or its corresponding prepolymer with the balance being solvent, additional mono- and polycyanato-group containing compounds, thermal curable or reactive compounds other than cyanate esters, cure accelerators and customary additives and fillers. Suitable solvents include ketones, such as methyl ethyl ketone, methyl isobutyl ketone, aromatic hydrocarbons, such as toluene or xylene, ethers, such as dioxane, tetrahydrofuran or ethylene glycol monomethyl ether, alcohols, such as methanol, ethanol, isopropyl alcohol, amides, such as dimethylformamide or dimethylacetamide and mixtures thereof. Aromatic hydrocarbons and ketones are preferred.

For casting applications, a thermosetting composition described above can be heated to a molten state to produce a prepolymer composition before casting into a mold, and then allowed to cure at an elevated temperature. For bonding applications, a resin varnish or molten prepolymer composition is applied to the surfaces to be bonded, and then allowed to cure under heat and pressure. Prepregs are produced by impregnating a suitable substrate with a resin varnish containing the inventive compound and drying the impregnated substrate. The impregnation apparatus can be of conventional design. Examples of substrates used in the preparation of prepregs include carbon fiber, glass fiber substrates, such as glass cloth or glass non-woven fabric, cellulosic substrates, such as kraft paper or cotton linter paper, synthetic fiber fabric such as aramide cloth or aramide nonwoven fabric. Composite laminates can be produced using different types of substrates in combination. The compounds and compositions disclosed herein can be utilized to produce aircraft interior section in known fashion, such as the interiors disclosed in U.S. Pat. No. 5,714,419, assigned on its face to Fiberite, Inc., which is incorporated herein by reference.

Microcombustion data for molded articles containing the inventive compounds were obtained using a pyrolysis-combustion flow calorimeter developed by the Federal Aviation Administration ("FAA"). In the test, 1 to 5 mg sample is placed in a 10-mm-long by 2.5-mm outside diameter quartz tube. A linear 10° C./second heating rate is used. The pyrolysis products are swept from the pyrolyzer by flowing nitrogen gas stream through a heated transfer line and mixed with excess oxygen prior to entering a high-temperature furnace to force complete combustion of the pyrolyzate. The heat release by combustion is calculated from the oxygen consumption using a universal value of 13.1 kJ of heat released per gram of diatomic oxygen consumed. The data of peak heat release rate and total heat release are obtained from the calorimeter on triplicate samples of each material measured.

The flammability resistance for the resin was also measured according to the Ohio State University heat release test (OSU test). This test measures the amount of heat evolved in a period of 2 minutes (C) as well as the rare of heat evolution at the peak (B) when a given test sample is exposed to radiation under specified conditions. OSU test results in a curve of heat evolution versus time. The rate of heat is increased at specified conditions according to the Federal Aviation Administration (FAA). This corresponds to the impingement of a sample at rate of 3.5 watts/cm$^2$. The volatiles are completely burnt by a small flame and the heat evolved is recorded as a function of time. Glass fabric does not contribute to heat evolution.

Several examples are set forth below to illustrate the nature of the invention and method for carrying it out. However, the invention should not be considered as being limited to the details thereof. All parts are in parts by weight unless otherwise indicated.

EXAMPLE 1

1,1-dichloro-2,2-bis(4-hydroxyphenyl)ethylene is prepared as follows

A 4-necked 3-L flask, equipped with a mechanical stirrer, a nitrogen inlet, and thermometer, is charged with 83% sulfuric acid (640 g). To this sulfuric acid, phenol (354 g) is added at 20° C. Chloral (200 g) in an additional funnel is added dropwise to the phenolic stirring mixture. The reaction temperature is maintained below 30° C. After the addition, the mixture is allowed to stir at room temperature for 18 hours, before water (640 g) is added. The resulting mixture is filtered and washed with more water to afford 1,1,1-trichloro-2,2-bis(4-hydroxyphenyl)ethane (423 g) as white solids.

A 4-necked 5-liter flask, equipped with a mechanical stirrer, a thermometer, and a condenser, is charged with methanol (800 g). Potassium hydroxide (440 g) is added in portions to the methanol solution. After the addition, the solution is cooled to 20° C. To this stirring solution, 1,1,1-trichloro-2,2-bis(4-hydroxyphenyl)ethane (420 g) is added in portions. The reaction temperature is kept below 40° C. After the addition, the temperature is raised to 50° C. and maintained for 2.5 hours. The reaction mixture is cooled to 20° C. and neutralized with 25% HCl solution. After the neutralization, the mixture is heated to reflux and water (480 g) is added. The mixture is allowed to cool to the room temperature. The precipitates are filtered and dried to afford 1,1-dichloro-2,2-bis(4-hydroxyphenyl)ethene as white solids with slight tan color.

EXAMPLE 2

1,1-dichloro-2,2-bis(4-cyanatophenyl)ethylene

A 4-necked 5-L flask, equipped with a mechanical stirrer, a thermometer, and an additional funnel, is charged with methyl isobutyl ketone (1500 g), 1,1-dichloro-2,2-bis(4-hydroxyphenyl)ethene (320 g), and cyanogen bromide (270 g). The resulting solution is cooled to −20° C. with a dry ice/acetone bath. To the stirring solution, triethylamine (240 g) in the additional funnel is added dropwise. The reaction temperature is maintained below −20° C. After the addition, the resulting mixture is allowed to warm up to 0° C. and quenched with dilute HCl aqueous solution. The organic layer is washed further with water a few times and concentrated under vacuum to afford 370 g of amber liquid, which solidifies as light tan color solids.

EXAMPLE 3
1,1-dibromo-2,2-bis(4-hydroxyphenyl)ethylene

A 4-necked 3-L flask, is equipped with a mechanical stirrer, a nitrogen inlet, and thermometer, is charged with 83% sulfuric acid (640 g) and phenol (354 g). To the resulting milky mixture, tribromoacetaldehyde (380 g) in an additional funnel is added dropwise. The reaction temperature is maintained below 30° C. After the addition, the mixture is allowed to stir at the room temperature for 18 hours, before water (640 g) is added. The resulting mixture is filtered and washed with more water to afford 1,1,1-tribromo-2,2-bis(4-hydroxyphenyl)ethane.

A 4-necked 5-liter flask, equipped with a mechanical stirrer, a thermometer, and a condenser, is charged with methanol (800 g). Potassium hydroxide (440 g) is added in portions to the methanol solution. After the addition, the solution is cooled to 20° C. To this stirring solution, 1,1,1-tribromo-2,2-(4-hydroxyphenyl)ethane (420 g) is added in portions. The reaction temperature is kept below 40° C. After the addition, the temperature is raised to 50° C. and kept for 2 hours. The reaction mixture is cooled to room temperature and neutralized with 25% HCl solution. After the neutralization, the mixture is heated to reflux and water is added. The mixture is allowed to cool to the room temperature. The precipitates formed are filtered and dried to afford 1,1-dibromo-2,2-bis(4-hydroxyphenyl)ethene.

EXAMPLE 4
1,1-dibromo-2,2-bis(4-cyanatophenyl)ethylene

A 4-necked 5-L flask, equipped with a mechanical stirrer, a thermometer, and an additional funnel, is charged with methyl isobutyl ketone (1500 g), 1,1-dibromo-2,2-bis(4-hydroxyphenyl)ethene (420 g), and cyanogen bromide (270 g). The resulting solution is cooled to −20° C. with a dry ice/acetone bath. To the stirring solution, triethylamine (240 g) in the additional funnel is added dropwise. The reaction temperature is maintained below −20° C. After the addition, the resulting mixture is allowed to warm up to 0° C. and quenched with dilute HCl aqueous solution. The organic layer is washed further with water several times and concentrated under vacuum to afford the desired product.

Other suitable halogenated co-curing agents are shown below.

11 cresol

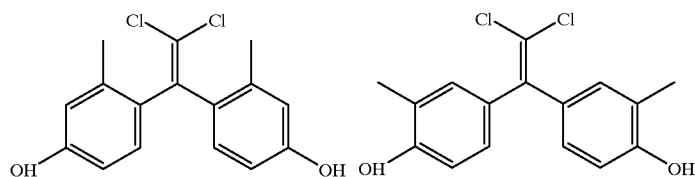

12 xylenil

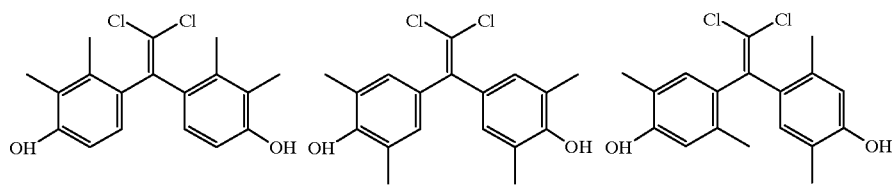

13 anthrol

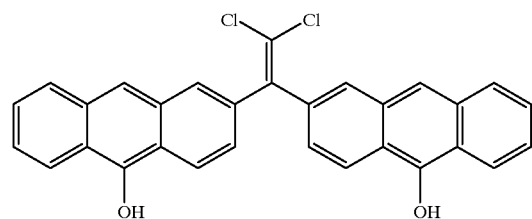

14 phenantrol

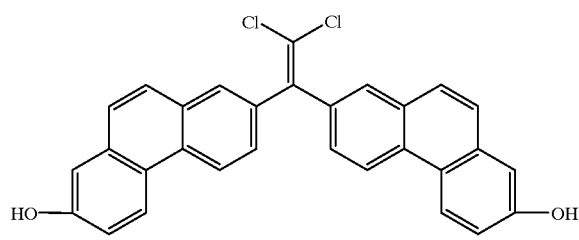

-continued
15 pyrocatechol
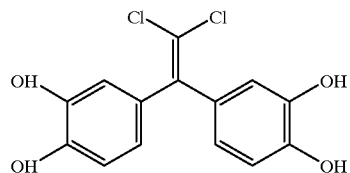
16 hydroquinone
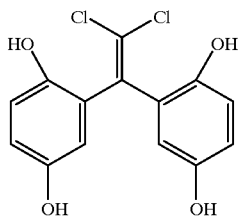
17 resorcinol
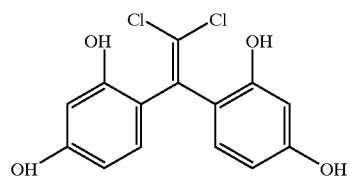
18 chlorophenol
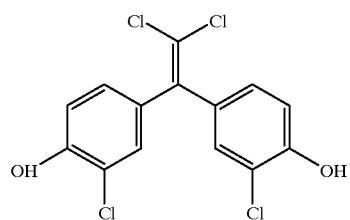
19 dichlorophenol
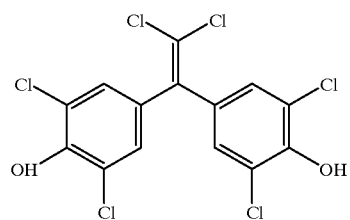
20 chlorohydroquinone
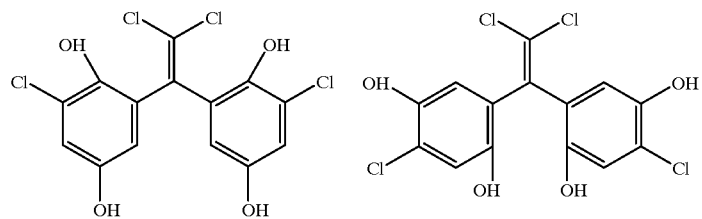
21 2,6-dichlorohydroquinone
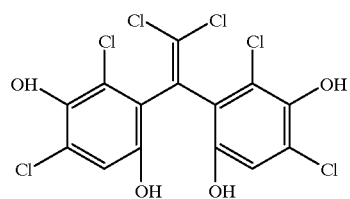

-continued 22 2,5-dichlorohydroquinone

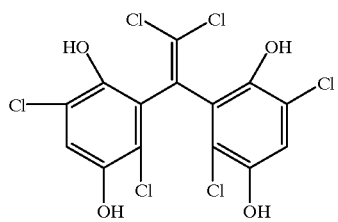

23 2,3,6-trichlorohyrdoquinone

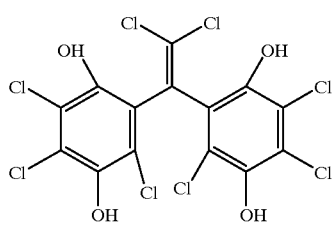

24 4-chlororesorcinol

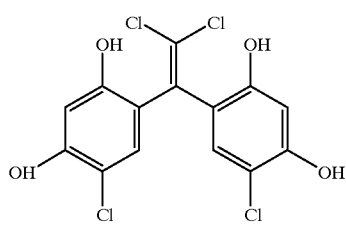

25 4,6-dichlororesorcinol

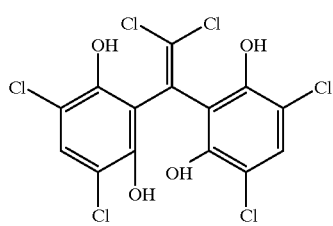

Application Examples

In aluminum dish, 12 g of the resin of example 1 and the following co-curing components listed in following table are mixed at 100° C. The resulting mixtures are cured at 150° C. for 30 minutes. The cured materials are studied for their heat release rate with the microcalorimeter developed by the Technical Center of FAA. The test was done on each sample in triplicate. The average values are listed in the table.

TABLE 1

Results of Micro Heat Release Study

| App. Example | Resin from example 2 | Naphthol | Resin from Example 1 | Peak Heat Release Rate Joule/g-°K | Total Heat Release KJoule/g |
|---|---|---|---|---|---|
| 1 | 100 | — | — | 8.0 | 1.8 |
| 2 | 100 | 15 | 0 | 17 | 3.7 |
| 3 | 100 | 12.5 | 0 | 15 | 3.8 |
| 4 | 100 | 10 | 0 | 14 | 3.2 |
| 5 | 100 | 10 | 2.5 | 14 | 3.3 |
| 6 | 100 | 10 | 5 | 10 | 2.4 |
| 7 | 100 | 7.5 | 7.5 | 10 | 2.3 |
| 8 | 100 | 5 | 10 | 10 | 2.4 |
| 9 | 100 | 0 | 15 | 9 | 2.2 |
| 10 | 100 | 0 | 17.5 | 9 | 2.4 |
| 11 | 100 | 2.5 | 15 | 9 | 3.1 |

Application Example 2

A number of ⅛ inch composite using glass or carbon fabric and resin are prepared. A predetermined size of glass or carbon fabric is uniformly coated with 60% wt solution of resin in acetone. The resin is prepared from the composition from application example 10. The prepreg are dried and 1 ply of the prepreg is stacked on each side of ⅛ inch Nomex honeycomb and the sandwich panel is cured in a hot press. Curing is carried out at 150–160C for 20 minutes. The cured laminates are weighed and the resin content is determined to be about 30–35%. The OSU test is carried out on each sample in triplicate. The average of three value is shown in

TABLE 2

OSU Test Results

| | Peak Heat Release Rate $KW/m^2$ | Total Heat Release $KW/m^{2-min}$ |
|---|---|---|
| Ex. 2a Nomex core with glass composite | 22.5 | 14.0 |
| Ex. 2b Nomex core with carbon composite | 23.6 | 14.0 |

Preferred embodiments of the present invention relating to novel aromatic cyanate esters, compositions thereof and methods for using the same have been described above.

Those skilled in the art having the benefit of the teachings presented in the foregoing will recognize modifications and other embodiments. Therefore, it is understood that the invention is not limited to the specific embodiments disclosed herein, and that modifications and other embodiments are intended to be within the scope of the appended claims.

We claim:

1. A composition of matter comprising a) a compound represented by formula (I):

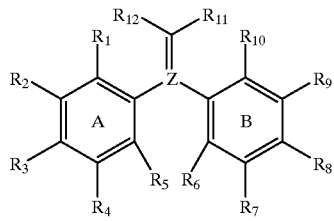

(I)

wherein
- Z is $C_1$–$C_4$ alkylene group or a five or six membered cycoalkylene; $R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
- $R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
- $R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or
- $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
- $R_{11}$ and $R_{12}$, independently of one another are H, phenyl, $C_1$–$C_4$alkyl or halogen;
- wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one cyanato group;

b) a co-curing component selected from the group consisting of
- b1) an aromatic compound having two or three carbon rings and at least one hydroxyl group per molecule;

b2) a compound according to formula II

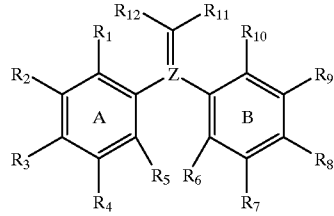

(II)

wherein
- Z is $C_1$–$C_4$ alkylene group;
- $R_1$, $R_5$, $R_6$ and $R_{10}$, independently of one another, are unsubstituted or halogen- or $C_1$–$C_3$alkyl-substituted $C_1$–$C_4$ alkyl that can be saturated or unsaturated, halogen, H, OCN, OH, $C_1$–$C_4$alkoxy, alkythio, mercaptan, nitro, —OCOR($C_1$–$C_3$alkyl), —NCOR ($C_1$–$C_3$alkyl), —COR, —$NO_2$, —NR'R", wherein R, R' and R" are H or $C_1$–$C_3$alkyl;
- $R_2$, $R_4$, $R_7$ and $R_9$, independently of one another, are $C_1$–$C_4$alkyl, halogen, H, OCN, or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl;
- $R_3$ and $R_8$, independently of one another, are $C_1$–$C_4$alkyl, halogen H, OCN or OH, $C_1$–$C_4$alkoxy, alkythio, mercaptan, nitro, —OCOR($C_1$–$C_3$alkyl), —NCOR($C_1$–$C_3$alkyl), —COR, —$NO_2$, —NR'R", wherein R, R' and R" are H or $C_1$–$C_3$alkyl; or
- $R_1$ and $R_2$ together and/or $R_2$ and $R_3$ together, and/or $R_9$ and $R_{10}$ together, and/or $R_8$ and $R_9$ together, independently of one another, form one or more aromatic rings or five or six membered cycloalkylene that can each be substituted with $C_1$–$C_4$alkyl or halogen;
- $R_{11}$ and $R_{12}$, independently of one another are H, phenyl, $C_1$–$C_4$alkyl or halogen;
- wherein at least one of aromatic rings A and B or at least one of the aromatic rings or the five or six membered ring formed by $R_1$ and $R_2$ and/or $R_2$ and $R_3$ and/or $R_9$ and $R_{10}$ and/or $R_8$ and $R_9$ is substituted by at least one hydroxyl group and at least one of $R_{11}$ and $R_{12}$ is a halogen group and b3) mixtures thereof.

2. A composition according to claim 1 wherein the compound of formula I is represented by
- Z is $C_1$–$C_2$alkylene;
- $R_1$ and $R_{10}$ are H;
- $R_2$, $R_4$, $R_7$ and $R_9$, independently of one another, are halogen, H, OCN, or OH;
- $R_3$, $R_5$, $R_6$ and $R_8$, independently of one another, are H, OCN or OH;
- $R_{11}$ and $R_{12}$ are halogen; and
- at least one of aromatic rings A and B is substituted by at least one cyanato group.

3. A composition according to claim I wherein the compound of formula I is represented by
- Z is $C_1$–$C_2$alkylene;
- $R_1$, $R_5$, $R_6$ and $R_{10}$ are H;
- $R_2$, $R_4$, $R_7$ and $R_9$, independently of one another, are halogen or H;

$R_{11}$ and $R_{12}$ are halogen; and $R_3$ and $R_8$ are OCN.

4. A composition according to claim 3 wherein $R_{11}$ and $R_{12}$ are chlorine or bromine.

5. A composition according to claim 4 wherein $R_{11}$ and $R_{12}$ are chlorine.

6. A composition according to claim 3 wherein

Z is methylene, $R_1$, $R_2$, $R_4$, $R_5$, $R_6$, $R_7$, $R_9$ and $R_{10}$ are H;

$R_3$ and $R_8$ are OCN; and $R_{11}$ and $R_{12}$ are chlorine.

7. A curable formulation comprising a) a composition according to claim 1 or a cyclotrimerized reaction product thereof and b) a thermally curable monomer or oligomer other than a cyanate ester.

8. A curable formulation according to claim 7 wherein the thermally curable or reactive monomer or oligomer is selected from an epoxy, bismaleimide, polyimide, polyester, epoxy-acrylate, urethane-acrylate, diallyl phthalate, spiropyrane, phenolic resin and mixtures thereof.

9. A cured article resulting from a composition according to claim 1 or a cyclotrimerized reaction product thereof having a peak heat release rate of less than about 20 Joule/g-°K as measured using a pyrolysis-combustion flow calorimeter developed by the Federal Aviation Administration.

10. A cured article resulting from a composition according to claim 1 or a cyclotrimerized reaction product thereof having a peak heat release rate of less than about 25 KW/m$^2$ as measured by the Ohio State University heat release test.

* * * * *